United States Patent [19]

Milman

[11] Patent Number: 5,256,768
[45] Date of Patent: Oct. 26, 1993

[54] EXPRESSION OF ANTIGENIC EPSTEIN-BARR VIRUS POLYPEPTIDES IN BACTERIA AND THEIR USE IN DIAGNOSTICS

[75] Inventor: Gregory Milman, Potomac, Md.

[73] Assignee: The Johns Hopkins University, Baltimore, Md.

[21] Appl. No.: 578,480

[22] Filed: Sep. 5, 1990

Related U.S. Application Data

[63] Continuation of Ser. No. 170,696, Mar. 14, 1988, abandoned, which is a continuation of Ser. No. 808,634, Dec. 13, 1985, abandoned.

[51] Int. Cl.$^5$ ............... A61K 39/245; C07K 15/04; C07K 13/00
[52] U.S. Cl. .................. 530/350; 530/402; 530/403; 530/806; 530/826; 424/89; 435/320.1
[58] Field of Search ............. 530/350, 402–403; 435/71.2, 69.7, 320.1; 424/89; 514/2

[56] References Cited

U.S. PATENT DOCUMENTS

| Re. 33,897 | 4/1992 | Vaughn et al. | 530/326 |
|---|---|---|---|
| 4,879,213 | 11/1989 | Fox et al. | 435/5 |
| 5,116,725 | 5/1992 | Vaughn et al. | 435/5 |
| 5,122,448 | 6/1992 | Vaughn et al. | 435/5 |

OTHER PUBLICATIONS

Proc. Natl. Acad. Sci. 80 7650–3 (1983).
Journal of Immunological Methods 63 (1983) 171–185.
Journal of Immunological Methods 67 (1984) 145–156.
Journal of Immunological Methods 67 (1984) 225–233.
Nature 310 (1984) 207–211.
Silhavy, et al., *Experiments with Gene Fusions* Cold Spring Harbor Lab. 1984, pp. 1–4, 7–11.
Int. J. Cancer 8, 272–282 (1971).
J. Virology (1983) 193–201 vol. 47.
Nature 313 (1985) 812–815.
Proceedings of the National Acad. Sciences 80 (1983) 5665–9.

*Primary Examiner*—Christine M. Nucker
*Assistant Examiner*—T. Cunningham
*Attorney, Agent, or Firm*—Rothwell, Figg, Ernst & Kurz

[57] ABSTRACT

Bacterially synthesized polypeptides that are recognized by antibodies produced in EBV-infected humans are disclosed. Plasmids containing DNA sequences encoding portions of the EBNA and EBEA-D antigens are also disclosed, as are methods for expressing these DNA sequences in bacteria. The DNA sequence encoding the EBNA-1-related fusion polypeptide is found in a Bam H1 K-restriction fragment, while that encoding the EBEA-D-related fusion polypeptide is found in a Bam H1 M-restriction fragment.

6 Claims, 7 Drawing Sheets

EXPRESSION OF ANTIGENIC EPSTEIN-BARR VIRUS POLYPEPTIDES IN BACTERIA AND THEIR USE IN DIAGNOSTICS

This application is a continuation of Ser. No. 07/170,696, filed Mar. 14, 1988, now abandoned, a continuation of Ser. No. 06/808,634, filed Dec. 13, 1985, now abandoned.

The present invention is concerned with bacterially synthesized antigenic polypeptides (BSAPs) which are recognized by human Epstein-Barr virus (EBV) antibodies. The invention also relates to the use of these BSAPs to provide a sensitive enzyme-linked immunosorbent assay (ELISA) which may be employed to effectively quantitate EBV antibodies. Such quantitation is useful in, for example, identifying EBV-related diseases such as infectious mononucleosis (IM) and nasopharyngeal carcinoma (NPC). Other uses are also hereinafter disclosed.

The work described herein was funded by grants from the National Insitute of Environmental Health Sciences, the National Institute of General Medical Sciences, and the National Institute of Allergy and Infectious Diseases.

BACKGROUND OF THE INVENTION

Epstein-Barr virus (EBV) is commonly present in humans. Antibodies to EBV polypeptides can be found in over 80% of human serum samples from the United States, and in even higher percentages from populations in Asian and African countries. In spite of its universal dominion, the consequences of EBV infection vary for different populations. Thus, for example, EBV is responsible for infectious mononucleosis (IM) in Western countries, and is implicated in Burkitt's lymphoma in Africa and nasopharyngeal carcinoma (NPC) in Asia. NPC is a major form of cancer in southern China where incidence rates are as high as 100 per 100,000 per year. The occurrence of these three EBV-associated diseases is rare other than in their normally associated populations. The risk-factors for different outcomes of EBV infection are not clear, although malarial infection in Africa and diet and use of medicinal herbs in Asia are potential co-factors.

There is a substantial amount of literature describing the serological screening for antibodies to EBV nuclear antigens (EBNA), early antigens (EA), and viral capsid antigens (VCA) in normal individuals and in patients with EBV-related diseases. EBNA is a viral product that is expressed in all cells carrying EBV DNA. Two separate components of EBNA have been identified by serology (see Proc. Nat'l. Acad. Sci., USA, 1983, 80: 5665–5669 AND 7650–7652). The major EBNA polypeptide is synthesized from the EBV BamHI K-restriction fragment and appears to be involved in the replication of EBV DNA as a plasmid (Nature, 1985, 313: 812–815).

Early antigens (EA) in Raji cells superinfected with EBV were first described as a complex of viral proteins that were expressed during the first 8–12 hours following infection (Science, 1970, 169: 188–190). The EA antigen complex consists of a "restricted" component (EA-R) and a "diffuse" component (EA-D) identified by their differential sensitivity to methanol and acetone fixation, sensitivity to proteases, and their location in the infected cells (Int. J. Cancer, 1971, 8: 272–282). The EA complex is among the first viral antigens to be expressed in lytic infection. The presence of antibodies to EA is considered to be an indicator of active viral production.

Antibody quantitation is generally determined by applying serially diluted serum samples to fixed smears of cells expressing, for example, EBNA, VCA or EA. Reactivity is detected by indirect immunofluorescence. An enzyme-linked immunosorbent assay (ELISA) for antibodies to EBV antigens, as provided by the present invention, offers the potential for an automated, highly-sensitive alternative to indirect immunofluorescence which does not require the experience or judgment of an expert technician.

Many investigators have described ELISA methods which employ crude or partially purified extracts of chemically induced cells to detect antibodies to early antigens. See Proc. Natl. Acad. Sci., USA, 1983, 80: 7650–7652; J. Infect. Diseases, 1982, 146: 734–740; J. Immunol. Meth., 1983, 63: 171–185 and J. Immonol. Meth., 1984, 67: 225–233. The development of monoclonal antibodies to early antigens (EA) enabled protein purification by affinity chromatography. Recently, Luka et al (J. Immunol. Meth., 1984, 67: 145–156) described an ELISA using EA-D purified by affinity chromatography using R3 monoclonal antibody (J. Virol., 1983, 47: 193–201) against the 50–52 kdalton EA-D protein. These workers harvested approximately 100 ug of partially purified EA-D per packed ml ($10^9$) of TPA (12-0-tetradecanolylphorbol 13-acetate) induced P3HR-1 cells. Such preparation of EA-D from tissue culture cells appears to be too expensive for use in mass clinical screenings.

A principal object of the invention is to provide a less expensive and otherwise more convenient source of EBV antigens for use in quantitating EBV antibodies. Other objects will also be evident from the ensuing description.

DESCRIPTION OF THE INVENTION

As noted, the present invention provides bacterially synthesized antigenic polypeptides (BSAPs) which are recognized by human EBV antibodies and can be used to provide a sensitive ELISA which is useful to quantitate EBV antibodies.

These BSAPs are prepared by using plasmids, particularly pHE6 plasmids containing Epstein-Barr virus (EBV) DNA which cause bacteria harboring the plasmids to produce the bacterially synthesized antigenic polypeptides (BSAPs) related to the antigens that EBV produces in man. These BSAPs are recognized by human EBV antibodies and, therefore, can be used to quantitate the immune response to EBV infection in man. Prior to the present invention, it was not known if EBV antigens could be synthesized in bacteria so as to be recognized by human antibodies.

The invention contemplates BSAPs related to EBV early antigens (EA), nuclear antigens (EBNA) and viral capsid antigens (VCA). High expression plasmids, e.g. pHE6 plasmid, suitable for the production of BSAPs according to the invention are described in the literature. See J. Biol. Chem. 258: 7469–7475 and 11571–11575 (1983), the contents of which are incorporated herein by reference and made a part of this disclosure. Bacterial synthesis using such plasmids, and the characterization of the thus synthesized EBNA polypeptide (BamHI K-EBNA), are also disclosed in the following papers, same being incorporated herein as part of the present disclosure:

(1) "Bacterially Synthesized EBNA as a Reagent for Enzyme Linked Immunosorbent Assays" by Milman et al in *Epstein-Barr Virus and Associated Diseases* volume of *Prog. Med. Virol*, Levine P, Ed (Martinus Nijhoff, Boston) 1985;

(2) "The Carboxylterminal Domain of the Epstein-Barr Virus Nuclear Antigen (EBNA-I) is Highly Immunogenic in Man" by Milman et al, *Proc. Natl. Acad. Sci. USA.* 82: 6300-6304 (1985); and (3) "Sequence Specific DNA Binding of the Epstein-Barr Virus Nuclear Antigen (EBNA) to Clustered Sites in the Plasmid Maintenance Region" by Milman et al, *Cell.* 42: 859-868 (1985).

As disclosed in *PNAS* 1985 and *Prog. Med. Virol.* 1985 above, the pHE6 constructs of the invention containing a 2236bp Sma I subfragment of EBV (p3HR-1) Bam H1 K fragment, when expressed in *E. coli* strains, produce EB-NA polypeptides as "run-on", i.e., fusion, proteins containing fragments of the λ bacteriophage N protein and linker, fused with amino acids from the carboxy terminus approximately one third of EB NA. This fusion protein should not be present in extracts of bacteria containing the EB-NA in the antisense orientation. By producing the desired EB-NA polypeptide fragment as a fusion peptide with the λ phage N protein, the stability of the thus-produced peptide may be increased and larger amounts of diagnostically useful protein produced. The resultant fusion polypeptides, which have masses of about 24 to 28 kDa, are produced in desirably high amounts when expressed in *E. coli* strains such as K-12 DH1, comprising from about 5% to about 10% of the total soluble bacterial protein. The portion of the fusion EB-NA polypeptide arising from λ phage N protein not only does not interfere with the ability of the polypeptide to interact with anti-EBV antibodies present in human serum, but is required in order for such interactions to occur. Increasing the coding sequence of EB-NA to attempt to produce a fusion peptide longer than the one-third of the C-terminus did not produce longer EB-NA in bacteria. (See example below) An ELISA using this bacterially synthesized EBNA has been used to quantitate antibodies in healthy individuals and in patients with infectious mononucleosis, rheumatoid arthritis, Burkitt's lymphoma, and nasopharyngeal carcinoma.

Using similar plasmids, bacterially synthesized EA-D has been expressed from the BMRF1 open reading frame in the EBV BamH1 M-fragment (see "DNA Sequence and Expression of the B95-8 Epstein-Barr Virus Genome", by Baer et al, *Nature*, 1984, 310: 207-211), and has been shown to react with the R3 monoclonal antibody against EA-D (see "Two of the Three Open Reading Frames in the Epstein-Barr Virus BamHI-M Fragment Code for Nuclear Antigens", *J. Virol.* 56: 860-866 (1985), in press). The contents of these papers are also incorporated herein by reference and otherwise made a part of the present disclosure as though fully set out herein.

As disclosed in *J. Virol.* 1985 above, bacterially synthesized segments of the EBV early antigen polypeptide encoded by pHE6 plasmid constructs containing a 4340bp BCl 1 to Bam H1 fragment of the EBV Bam H1 M-fragment BMRF1 open reading frame are produced as a family of polypeptides of 46 to 55 kDa mass in which the normal initiator methionine residue of the BMRF1 protein is linked to an N-terminal segment of the λ bacteriophage N protein. These fusion polypeptides, following purification, may be used in rabbits to generate anti-BMRF1-specific antiserum. In addition, such fusion polypeptides can be identified as EB-EA-D by reaction in the R3 monoclonal antibody against EB-EA-D (diffuse subset of EA—Hennessy et al., *Proc. Nat'l. Acad. Sci.*, 80:5665 (1983)), and used in ELISA assays with human sera (see examples below).

The invention is further exemplified herein by reference to the preparation of the bacterially synthesized EBV antigens and their use in ELISA methods in the serological screening of a healthy North American population, North American patients with IM and Asian patients with NPC.

EXAMPLE

Methods and Materials (a) Bacterially Synthesized EBV Antigens

The 4339 bp BclI to BamHl fragment (bases 79894 to 84233 of the EBV genome (see *Nature*, 1984; 310 207-211) located within the EBV BamH1 M-fragment was inserted into the high expression plasmid pHE6 described in *J. Immunol. Meth.* 1983; 63: 171-185 and *Proc. Natl. Acad Sci.* 82: 6300-6304, at 6301, USA, 1985. The resulting plasmid pEAD causes the bacterial synthesis of EA-D coded in reading frame BMRF1. Bacterial extracts containing EA-D were prepared by a modification of the induction procedures described by Waldman et al (*J. Biol. Chem.*, 1983, 258 (11571-11575)) and EA-D polypeptide was purified by DEAE cellulose and phosphocellulose column chromatography.

In one embodiment, a 4340bp BCl 1 - Bam H1 subfragment of Bam H1-M fragment containing the complete EMRF1 reading frame was inserted, in phase, into a modified *E. coli* expression plasmid pHE6 at the Bam H1 site (plasmid pHE7). The resulting construct synthesized the BMRF1 polypeptide as a run-on product, fused to the bacteriophage λ N protein. Although the BMRF1 reading frame theoretically codes for a polypeptide of approximately 45 kDa, a 47 kDa fusion polypeptide was expressed, identified by immunoreaction with EBV-positive human serum, purified by column chromatography from the bacterial cultures, and inoculated into rabbits to generate antisera specific for the product of BMRF1 reading frame. When this anti-BMRF1 rabbit serum was incubated with Raji or B95-8 lymphoblastoid cells previously engineered to contain EB-EA coding regions, immunofluorescene assays detected a family of expressed polypeptides (46, 48, 50, 51,52,53 and 55 kDa) in cell extracts, the 2 major species being the 48- and 50-kDa fusion polypeptides. The R3 monoclonal antibody of Pearson et al., *J. Virol.* 47:193-201 (1983), which is known to immunoprecipitate the in vitro translation product of an RNA hybrid selected by Bam H1 fragment M and which is known to recognize 50- and 52-kDa polypeptides of the EA complex, identified the same fusion polypeptide complex in lymphoblastoid cells as did the aforementioned rabbit monospecific antiserum. It was determined that, in the aforementioned fusion polypeptides, the normal methionine residue of the BMRF1 protein was linked to an N-terminal 33 amino acid segment of the λ bacteriophage N protein, resulting in a 47-kDa specie. Cho et al., *J. Virol.* 1985, above.

The bacterial synthesis of a K-EBNA polypeptide is described by Milman et al in the *Epstein-Barr Virus and Associated Diseases* volume of *Prog. Med. Virol* (Martinus Nijhoff, Boston) 1985 and in *Nature*, 1985, 313:

812-815, referred to above and incorporated herein by reference.

In one example (PNAS, 1985, above), this plasmid system produced a 28 kDa fusion polypeptide that contained the C-terminal one-third of EB-NA and lacked the Cly-Cly-Ala repeat region that is known to produce polypeptides, antisera to which cross react with other cellular proteins. Luke et al., *J. Virol.* 52:833 (1984). The 28 kDa fusion polypeptide contained 36 amino acids from the bacteriophage N protein and linker and 191 amino acids from the carboxy terminus of EB-NA. Inactivation of the temperature sensitive regions in bacteria containing pNAK28 induced the synthesis of a 28 kDa fusion polypeptide which was the dominant band detected by Coomassi blue staining after Na Dod-SO$_4$/PAGE of crude bacterial extracts. After purification on phosphocellulose (elution between 0.5–0.6M NaCl) and hydroxyapatite (elution between 120–160 mM phosphate), the 28 kDa fusion fragment of EB-NA comprised about 8% of the soluble protein in bacterial extracts and was the only band recognized by EB-NA-positive human serum in immunoblots, thus confirming that it represented the produce of the inserted EB-NA coding region. Antibodies against the 28 kDa fusion polypeptide were produced in rabbits (monospecific) and mice (monoclonal).

The following plasmids have been deposited at the American Type Culture Collection, Rockville, Md.: plasmid pNAK28 (ATCC Accession No. 67070) encoding the EB-NA fusion polypeptide, and plasmid pEAD (ATCC Accession No. 67069) encoding the EB-EA-D fusion polypeptide.

(b) Human Serum Samples

Sera from 100 healthy North American volunteers were examined for expression of antibodies to EA-D. These sera had been previously characterized for antibody to EBNA by Milman et al in the papers referred to above in (a).

Another collection of 194 coded serial serum samples was obtained from 40 IM patients. Between 3 and 10 samples were available for each patient. The first sample was obtained an average of 9 days post-onset of disease. Subsequent samples were obtained at variable times ranging from 1 month to over 3 years later.

A collection of 288 coded serial serum samples from 48 Chinese patients with pathologically confirmed undifferentiated NPC was obtained from a serum bank maintained by the National Cancer Institute. The samples were collected from patients diagnosed with NPC. The age and sex of each patient were recorded, and each patient was assigned to Stage I, II, III, or IV, indicating the extent of the disease at the time of diagnosis. The first sample for each patient was obtained at the time of diagnosis, and subsequent samples were generally obtained 4 to 6 months thereafter for 2 or more years or until the patient died or was lost to follow-up. The number of serial samples per patient ranged from a minimum of 2 (6 patients) to a maximum of 11 (5 patients).

The correlations of clinical data with coded samples were made only after the ELISA characterizations were complete.

(c) Characterization of Bacterially Synthesized Antigen

Samples of purified EA-D were subjected to sodium dodecyl sulfate (SDS) polyacrylamide gel electrophoresis and stained with Coomassie Blue or electrophoretically transferred to nitrocellulose for immunoblot analysis. Nitrocellulose blots were washed in a solution of phosphate buffered saline (PBS) containing 0.05% Tween 20 and 2% normal goat serum (PBSTG) for two hours and then incubated for 6 hours with serum from an NPC patient diluted 1:100 in PBSTG. The blots were washed and then incubated for two hours with horseradish peroxidase-conjugated goat anti-human IgG (Fc specific), diluted 1:500 in PBSTG. The blots were washed overnight and then rinsed with PBS prior to addition of peroxidase substrate, 4-chloro-1-naphthol.

(d) Enzyme-Linked Immunosorbent Assay—ELISA

The purified EA-D was diluted to 2.1 ug/ml in 0.5 M sodium carbonate (pH 9.6) and 100 ul/well was applied to 96-well microtiter plates. The plates were incubated for 60 min at 37° C. and then washed with PBST (PBS containing 0.05% Tween 20). The wells were then filled with PBSTG to block non-specific binding sites and incubated for 60 min at 37° C. The solution was removed and 100 ul samples of test sera serially diluted by two-fold steps in PBSTG were added to the wells. The plates were incubated at 37° C. for 90 min; the sera removed; and the wells then washed 10 times with PBST. The wells were each filled with 100 ul of horseradish peroxidase-conjugated goat anti-human IgG (Fc specific) diluted 1:2000 in PBSTG and incubated for 40 min at 37° C. The plates were washed 8 times with PBST, and 100 ul of peroxidase-substrate (0.4 mg/ml O-phenylenediamine in 50 mM Tris-HCl (pH 3.2), 10 mM EDTA, and 0.01% H$_2$O$_2$) were added per well. The plates were incubated for 20 min at room temperature in the dark. The reactions were terminated by the addition of 50 ul/well of 4 N H$_2$SO$_4$. Absorbence at 492 nm was measured with a Titertek Multiscan MC.

Standard concentration curves for human IgG were generated by the above procedure after absorbing microtiter plates with purified human IgG in 2-fold dilutions from 25.0 to 0.78 ng/well in 0.5 M carbonate buffer, pH 9.6. Absorbance curves were consistently linear between 1.9 ng and 15.2 ng IgG/well, corresponding to Od$_{492}$ readings between 0.25 and 1.3, respectively.

Serum titer was defined as the reciprocal of the dilution that yielded an OD$_{492}$ closest to 0.7 which corresponds to an IgG concentration of approximately 50 ng/ml. Each serum sample was tested in duplicate. Postive control serum (from a patient with NPC) and negative control serum (from a healthy volunteer who was EBV seronegative by immunofluorescence for EBV viral capsid antigen) were applied as controls in each microtiter assay.

(e) Statistical Analysis

The Student's two-tailed T-test was used to determine the statistical significance of differences in geometric mean titers between groups. Survival analysis curves were constructed using a computer program which generates Kaplan-Maier survival curves.

RESULTS

(a) ELISA Using Bacterially Synthesized Antigens

Approximately 4 mg of purified EA-D was obtained per liter of bacterial culture. This amount of EA-D is sufficient for 360 96-well microtiter plates which allows the determination of anti-EA titers for approximately 4500 individuals.

DEAE and hydroxyapatite column chromatography of the crude bacterial extract resulted in an antigen preparation that was enriched approximately 90-fold for EA-D (FIG. 1). Although *E. coli* proteins were present in the EA-D antigen preparation, ELISA results using EBV negative sera and immunoblotting results using either NPC sera or EBV negative sera (FIG. 1) showed that the contaminating *E. coli* proteins were not recognized by human sera and further purification was not necessary for ELISA studies.

The inter-assay and intra-assay coefficients of variation (CV) for the EA-ELISA were 12% and 8%; and for the EBNA-ELISA were 10% and 8%, respectively. The mean titer of 12 EBV-VCA negative individuals was 34 (range 10–50) for EA, and 18 (range 10–20) for EBNA.

(b) Anti-EA and Anti-EBNA Titers in a Healthy North American Population

The distribution of anti-EA and anti-EBNA titers in a healthy North American population is illustrated in FIGS. 2 and 3. The anti-EBNA antibody levels showed a wide distribution. The median value for anti-EBNA IgG antibody titer was 400, and 96% of the population had titers under 10,000. Seventy per cent of the individuals had low, but detectable, antibodies to EA-D. The median value for anti-EA IgG antibody titer was 200 and 96% of the population had titers less than 1600.

(c) Anti-EA American Infectious Mononucleosis Patients

The highest anti-EA antibody level in IM patients was always observed in the earliest sample The distribution of anti-EA titers in initial samples is illustrated in FIG. 4. The median value for anti-EA IgG antibody titer was 1600 and the initial titers of 55% of the patients exceeded the titers of 96% of the healthy North American population. By six months post-infection, the anti-EA titers of all IM patients decreased to levels seen in the healthy population. All further samples from IM patients (up to 2 years post-infection) contained a low but detectable level of anti-EA antibodies.

In the sera samples from the 43 IM patients, low but detectable levels of anti-EBNA antibodies (titers between 1/50 and 1/200) were observed for 26 patients (53%) at presentaton (4–73 days post onset) and for 30 patients (70%) during the first 6 months post-infection. After 6 months, all IM patients had low, but detectable, levels of anti-EBNA antibodies. In general, anti-EBNA titers of the IM patients remained low during the period of study and did not approach the levels observed either in the sera from high titer individuals in the healthy population or in sera from NPC patients.

(d) Initial Anti-EA and Anti-EBNA Titers in NPC Patients

The correlation between initial anti-EA titers for NPC survivors and non-survivors with stage of disease is illustrated in FIG. 5. There was an increase in the median anti-EA titer with more advanced stages of disease, but a large overlap existed between anti-EA titers of NPC patients assigned to different stages. The median titers appeared higher for non-survivors compared to survivors but the differences were not statistically significant.

The relation of initial anti-EBNA titers for NPC survivors and non-survivors with stage of disease is illustrated in FIG. 6. There appeared to be no significant difference in anti-EBNA antibody levels between survivors and non-survivors or between stages.

Correlation between survival and non-survival with highest observed titers for anti-EA in FIG. 7, and for anti-EBNA in FIG. 8 gave results similar to those obtained with initial titers. There was an increase both in anti-EBNA and anti-EA median titers for non-survivors compared with survivors. However, the overlap in values precludes using the measurements as prognostic indicators for an individual patient.

The probability of survival for an NPC patient as a function of time after the initial titer measurement was determined using Kaplan-Maier analysis. The patients were separated into two groups depending on changes in anti-EA antibody levels during the first twelve months following diagnosis. One group contained those who showed an increase in EA-D titer; the other, contained those who showed a constant EA-D titer or a decrease in EA-D titer. Each data point in FIG. 9 indicates the last sample obtained from a patient. Data points were superimposed when more than one last sample occurred at the same time. A last sample was obtained due to death (data points on vertical lines) or due to loss of follow-up information (data points on horizontal lines). The Kaplan-Maier analysis assumes that the probability of survival is the same for individuals for whom there is no follow-up information as it is for individuals for whom there is data.

The probability of survival showed a significant correlation ($p<0.02$) with the change in titer during the first 12 months after diagnosis. Those patients whose titers increased during this period had a significantly poorer probability of survival than patients whose titers remained constant or decreased. In fact, the probability of survival was 75% for patients whose titers decreased or remained constant, and near 0% for patients whose titers increased. The results were qualitatively the same for patients regardless of initial stage assignment or initial antibody titer.

The data set out above shows that serological screening for anti-EBV antibodies can be used to infer an EBV-related disease. The specific disease depends upon the population at risk. Since most individuals possess antibodies to EBV antigens, an accurate quantitation of the immune response provides the information which is critical for evaluation. In this regard, the antibody measurements obtained by the present ELISA method are at least 10-fold more sensitive than immunofluorescence procedures and are not influenced by subjective interpretations.

Quantitation of antibodies to EBNA have not been clinically useful in predicting disease, although the absence of antibodies to EBNA is characteristic of early stages of IM and certain immunodeficient diseases such as ataxia-telangiectasia. The wide distribution of anti-EBNA antibody levels in the healthy North American population suggests little correlation between anti-EBNA immune response and clinical disease although as a group, the NPC patients have higher levels of anti-EBNA antibodies. Since EBNA appears to be present in all cells containing EBV DNA, an individual's immune response to EBNA may be an indication of the number of EBV-transformed cells, i.e., high anti-EBNA titers result from high numbers of EBV-transformed cells. The higher levels of anti-EBNA antibodies in NPC patients would then be consistent with high numbers of EBV-transformed cells being a risk-factor for carcignogenesis.

Antibodies to EA are indicative of active EBV replication. It has previously been reported, using an immunofluorescence assay, that anti-EA antibodies were detectable in 75% of patients during the acute phase of infectious mononucleosis but dropped to non-detectable levels within a few months. Anti-EA antibodies were detected in only 12% of sera from individuals 4 to 8 years following infectious mononucleosis. Using the present ELISA measurements, antibodies to EA-D have been detected in 70% of the healthy North American population. There appears to be no correlation between the level of anti-EA antibodies and the level of anti-EBNA antibodies, suggesting that active viral production may not be linked to the number of EBV-transformed cells. The increased sensitivity of the present ELISA procedure compared to an assay based on immunofluorescence makes it possible to conduct studies which were previously not possible. For example, if the amount of anti-EA antibodies is an indication of the level of EBV production, then individuals with high anti-EA titers may actively shed virus. This predication may be quantitatively tested using a EBV DNA hybridization assay.

Confirmation of a diagnosis of IM by the heterophile assay is difficult or impossible for some patients, especially children. IM patients expressed non-detectable to low levels of anti-EBNA antibodies (FIG. 4). Therefore, an observation of high anti-EA antibody levels coupled with non-detectable or low anti-EBNA antibodies would be consistent with an IM diagnosis. Among the IM patients studied, 100% had measurable anti-EA antibodies and 55% had anti-EA antibody levels greater than two standard deviations above the geometric mean titer of the control population. Thus, EA-D titers above 1600 may suggest IM in Western populations. The significance of the wide range in the initial IgG response to EA-D among IM patients is not clear, but may reflect the variability in the inate ability of patients to respond to viral antigens, the time at which the samples were obtained relative to the progression of viral replication, or a variable level of viral replication within individuals.

In order to determine the clinical value of the ELISA procedures for patients with NPC, the initial antibody levels, peak antibody levels, and changes in antibody levels were examined for correlation between stages of disease at presentation and survival of the patients. In the studies involved, 75% of the NPC patients had higher anti-EA IgG antibodies than the healthy North American population. Although a better comparison would be with a healthy Asian population, the data are in agreement with that given in the literature and indicate that ELISA screening would be diagnostically useful in areas of high NPC incidence. The initial or peak levels of anti-EA antibodies appeared higher for groups of non-survivors compared to survivors, but the differences were not significant and had no predictive value for an individual patient.

It will be recognized that an assay which provides a prognosis indicating the effectiveness of treatment is useful for managing NPC patients. High levels of specific IgG antibodies to EA-D and IgA antibodies to VCA are found in Asian patients with undifferentiated NPC, suggesting that active viral replication is either associated with or closely precedes NPC. Based on an observed rise in anti-EA titer with increase in total tumor burden and a decrease in titer when the tumors appeared to be eradicated, it has previously been proposed that anti-EA determinations might serve to monitor the success of radiation therapy. Effective treatment should eliminate viral production and increases in the immune response to EA-D. This prediction was confirmed in case studies of Chinese patients described in the literature, and in studies of Japanese patients described by others. No statistical analysis was reported in either study, but the trends were clear. Thus, six out of eight patients who died had elevated EA titers at 12 months, and of the patients who survived, seven out of ten showed decreasing titers and three had unchanging titers to EA. Fewer cases, but similar results, were obtained in the Japanese study.

ELISA determinations of anti-EA antibody changes in serum samples from 42 Asian NPC patients made with the present invention are consistent with previous literature reports. As indicated in FIG. 9, the relative change in anti-EA antibody level was significantly correlated with survival. Decreasing titers to EA-D predict survival and increasing titers to EA-D predict an unfavorable course of NPC. By contrast, little or no changes with time were observed for anti-EBNA antibody levels for all patients.

The predictive value of monitoring the time dependence of anti-EA antibody levels is different from that provided by the antibody-dependent cellular cytotoxicity (ADCC) assay. The ADCC assay was developed to detect serum antibodies against cells expressing Epstein-Barr virus antigens. ADCC titer is directly correlated with survival of North American patients with non-keratinizing or undifferentiated NPC. However, high and low ADCC titers do not appear to depend upon stage at diagnosis or to change for an individual patient during the course of the disease. Therefore, ADCC appears to measure the ability of an individual's immune system to cope with NPC and is perhaps an indicator of the genetic background of the individual rather than a useful prognostic measurement of the success of therapy.

In summary, the present ELISA method for quantitation of levels of serum antibodies against EBV proteins is ideal for large-scale clinical diagnostics. The results obtained indicate that the ELISA data may be diagnostic for IM and NPC, and prognostic for the course of the diseases. Although the studies involved utilized a specific probe to IgG, specific probes for IgA or IgM should also be useful. A limitation of ELISA compared to immunofluorescence measurements is the requirement for an inexpensive source of antigen. The bacterially synthesized EBV polypeptides of the invention provide a low-cost source of antigen which makes the ELISA feasible.

While the drawings have been referred to in the foregoing, the following brief summary thereof is also provided in further explanation thereof:

FIG. 1 is a characterization of bacterially synthesized EA, the various lanes representing the following:

Lane A. Gel electrophoresis—polypeptides in the phosphocellulose fraction of bacterially synthesized EA-D were separated by SDS polyacrylamide gel electrophoresis and stained with Coomassie blue;

Lane B. Immunoblot—following gel electrophoresis, the polypeptides were electrophoretically transferred to nitrocellulose and probed with serum from an NPC patient to identify the location of EA-D polypeptides; and Line C. Immonoblot—same as in Lane B using serum from a healthy North American individuals who is sero-negative for antibody to EBV VCA.

Figure 1:
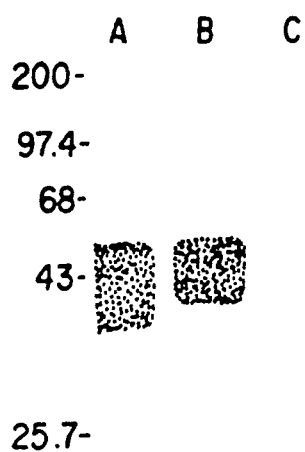
Figure 2:
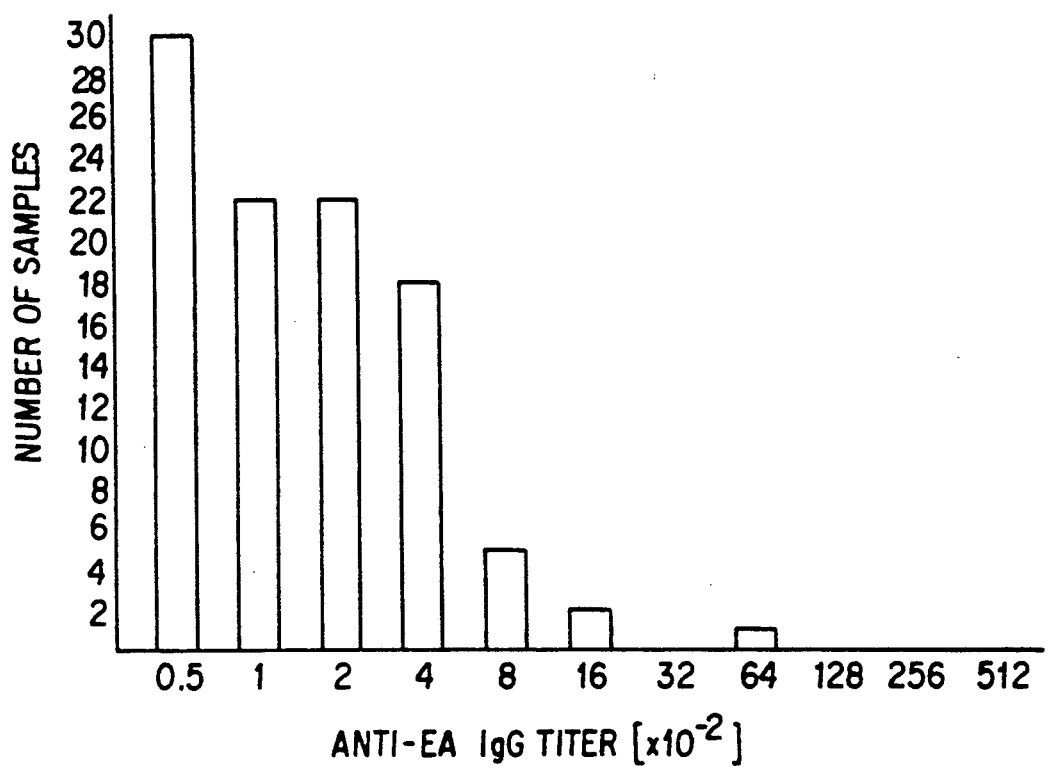
FIG. 2 shows the distribution of anti-EA IgG ELISA titers in a healthy North American population (N=100)
Figure 3:
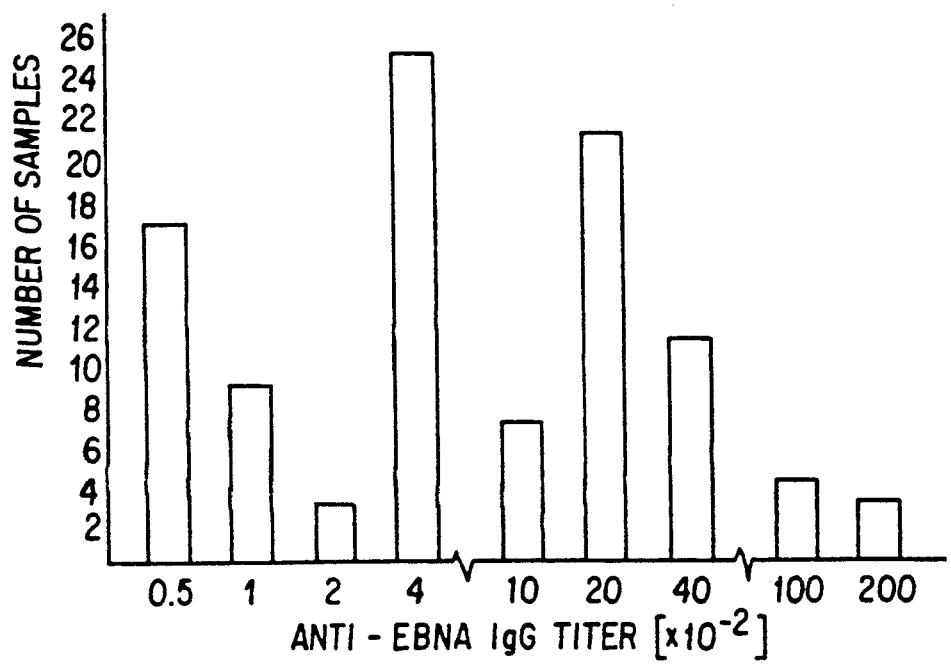
FIG. 3 illustrates the distribution of anti-EBNA IgG ELISA titers in a health North American population (N=100)
Figure 4:
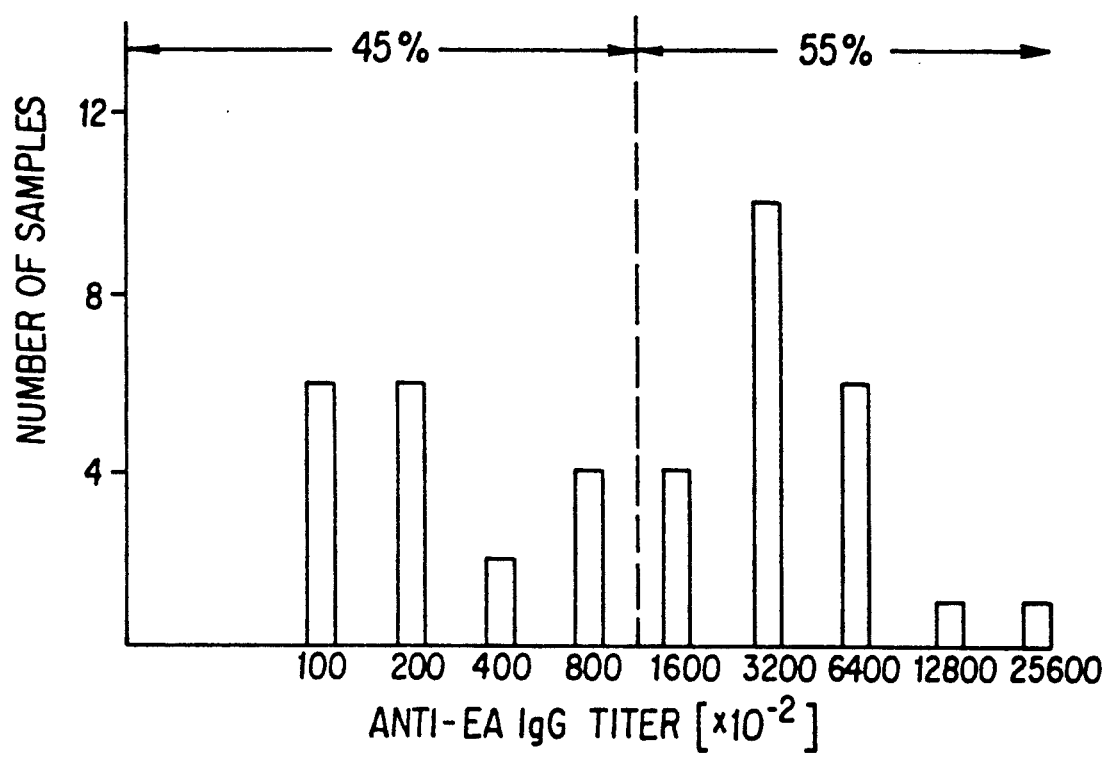
FIG. 4 represents the distribution of anti-EA IgG ELISA titers in the initial samples from patients with acute infectious mononucleosis (N=40)
Figure 5:
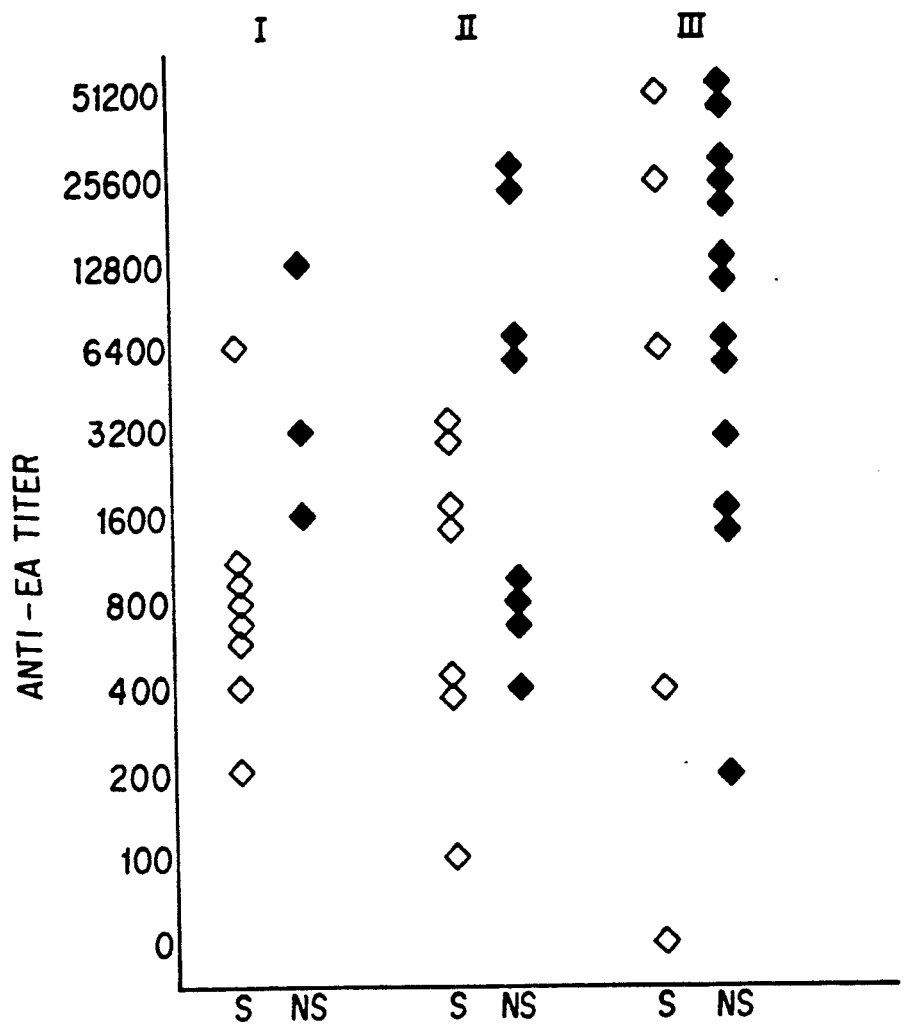
FIG. 5 shows the initial anti-EA IgG ELISA titers of NPC patients presenting with Stage, I, II, or III of the disease (N=46). Patients in each stage were subdivided into those that survived (S, open symbols) and those that died from NPC (NS, closed symbols)
Figure 6:
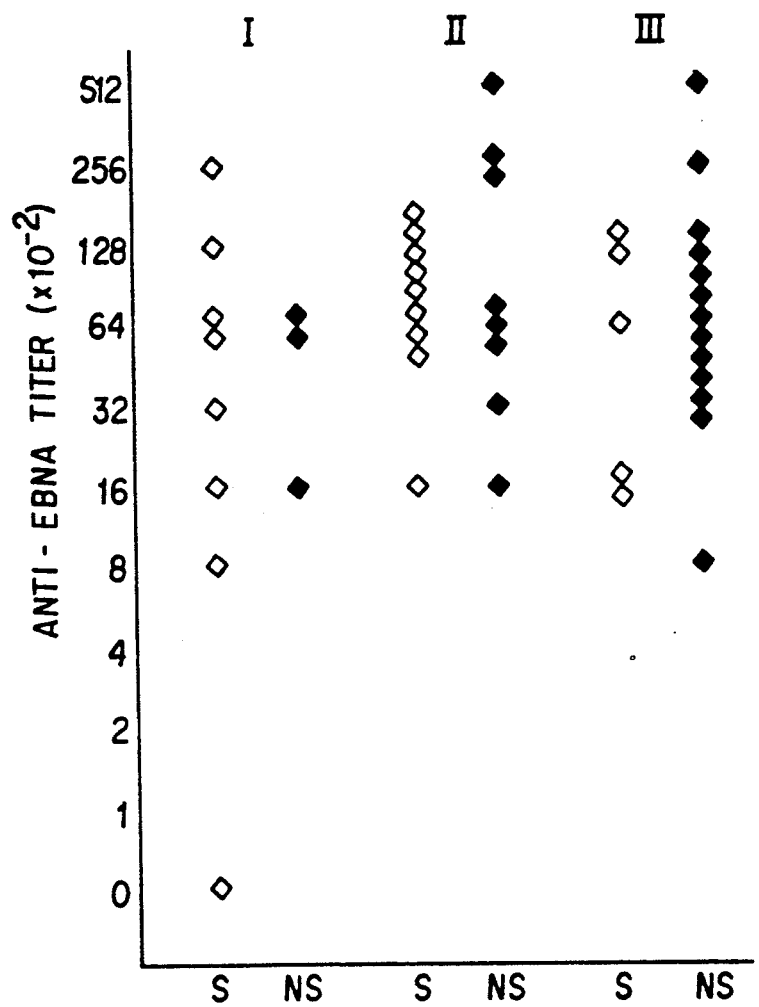
FIG. 6 shows the initial anti-EBNA IgG ELISA titers of NPC patients presenting with Stage I, II, or III of the disease (N=46). Patients in each stage were subdivided into those that survived (S, open symbols) and those that died from NPC (NS, closed symbols)
Figure 7:
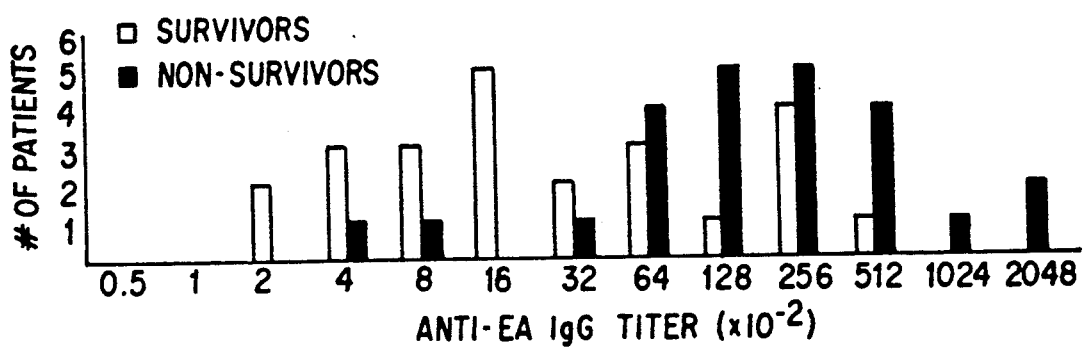
FIG. 7 illustrates the distribution of the highest observed anti-EA IgG ELISA titer for each NPC patient (N=46)
Figure 8:
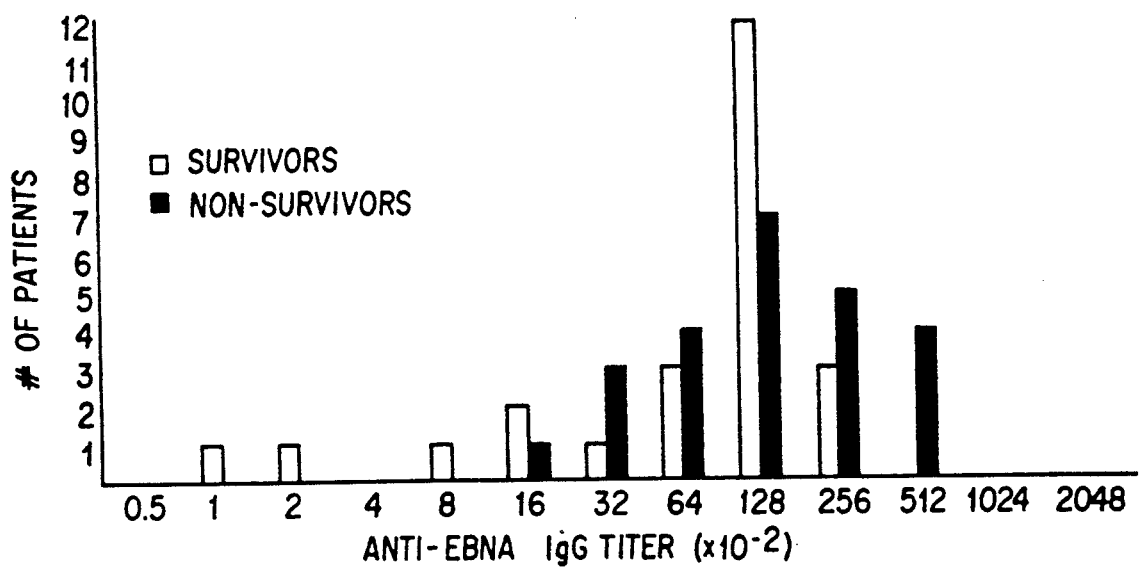
Figure 9:
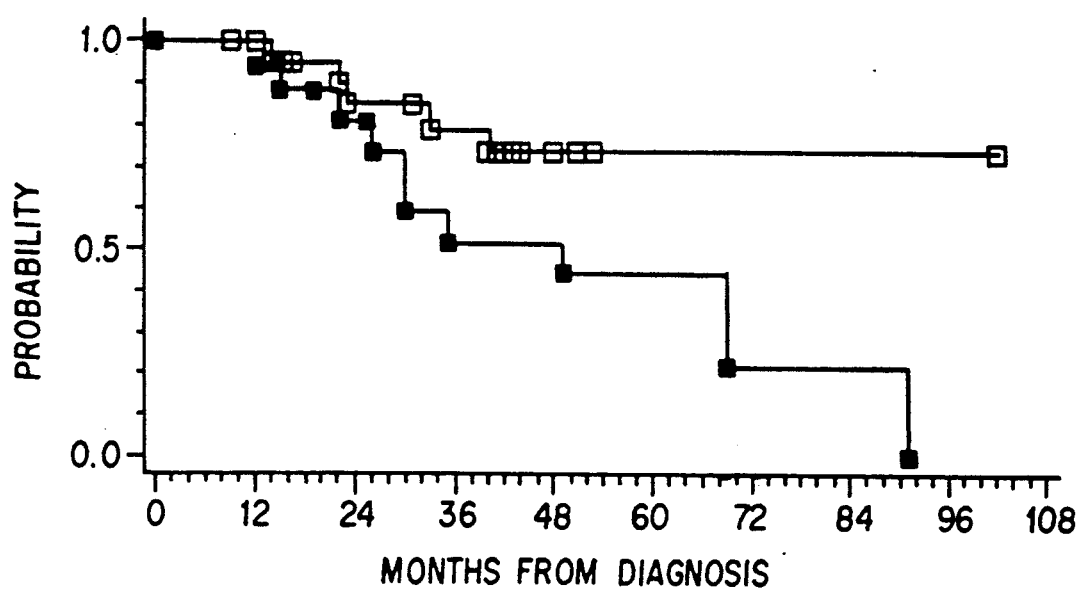

FIG. 8 illustrates the distribution of the highest observed anti-EBNA IgG ELISA titer for each NPC patient (N=46); and FIG. 9 shows the probability of survival as a function of time and change in anti-EA IgG ELISA titers within the first 12 months post-diagnosis. Only patients who survived longer than 12 months post-diagnosis, and who had samples taken 12 months or later post-diagnosis were included in the analysis (N=40). Patients were divided into two groups; those that showed an increasing antibody level to EA and those that showed a decreasing or no change in antibody levels against EA.

In summary, it will be appreciated that the invention, in its broadest aspects, contemplates the provision of bacterially synthesized antigenic polypeptides related to the antigens that EBV produces in man. These BSAPs are recognized by human antibodies. Prior to the invention, it was not known that EBV antigens could be synthesized in bacteria that would be recognized by human antibodies. The invention contemplates BSAPs related to EBV early antigens (EA), nuclear antigens (EBNA) and viral capsid antigens (VCA). These BSAPs can be used, as noted, to provide an ELISA for the purpose of quantitating the immune response to EBV infection in man. Such quantification is useful for clinical evaluations and in the treatment of EBV related diseases such as infectious mononucleosis, chronic mononucleosis, Burkitt's lymphoma and nasopharyngeal carcinoma. Detection of EBV reactivation is also important in organ and bone marrow transplants. In addition, the assays enable studies such as the evaluation of possible linkage between EBV and rheumatoid arthritis. ELISA assays require an inexpensive source of antigen and the BSAPs described herein provide such a source.

It will be appreciated that the enzyme-linked immunosorbent assay of the invention may be included as a part of a diagnostic assay kit of otherwise conventional structure and composition e.g. an ELISA plate containing the absorbed antigen and the reagents necessary to conduct the test.

Various modifications may be made in the invention described herein. Accordingly, the scope of the invention is defined in the following claims wherein:

I claim:

1. A bacterially synthesized polypeptide encoded by the Epstein-Barr Virus BamH1 K-fragment consisting essentially of the carboxyl-terminated one third of the Epstein-Barr Virus Nuclear Antigen ("EB-NA"), said polypeptide being recognized by human antibodies to nuclear antigens of Epstein-Barr Virus.

2. The polypeptide of claim 1 consisting of a 28 kDa fusion polypeptide encoded by plasmid pNAK28, said plasmid deposited under ATCC Accession No. 67070.

3. A bacterially synthesized polypeptide consisting essentially of the amino acid sequence encoded by the 4339 base pairs of the Bcl-1 to BamH1 restriction subfragment of the Epstein-Barr Virus BamH1 M-fragment said polypeptide being recognized by human antibodies to early antigens of the Epstein-Barr Virus.

4. The polypeptide of claim 3, encoded by plasmid pEAD, said plasmid deposited under ATCC Accession No. 67069.

5. Plasmid pNAK28 (ATCC Accession No. 67070).

6. Plasmid pEAD (ATCC Accession No. 67069).

* * * * *